United States Patent
Levine

(10) Patent No.: US 9,636,110 B2
(45) Date of Patent: May 2, 2017

(54) STRUCTURAL SUPPORT INCORPORATING MULTIPLE STRANDS

(71) Applicant: Alpha Scientific Corporation, Malvern, PA (US)

(72) Inventor: Marshall S. Levine, Wayne, PA (US)

(73) Assignee: ALPHA SCIENTIFIC CORPORATION, Malvern, PA (US)

( * ) Notice: Subject to any disclaimer, the term of this patent is extended or adjusted under 35 U.S.C. 154(b) by 442 days.

(21) Appl. No.: 13/815,666

(22) Filed: Mar. 13, 2013

(65) Prior Publication Data

US 2014/0275750 A1   Sep. 18, 2014

(51) Int. Cl.
| | | |
|---|---|---|
| A61B 17/04 | (2006.01) |
| A61B 17/06 | (2006.01) |
| A61B 17/00 | (2006.01) |
| A61B 90/00 | (2016.01) |

(52) U.S. Cl.
CPC ............ *A61B 17/06166* (2013.01); *A61B 2017/00792* (2013.01); *A61B 2017/06176* (2013.01); *A61B 2090/3925* (2016.02); *A61B 2090/3966* (2016.02)

(58) Field of Classification Search
CPC .... A61B 17/06166; A61B 2017/06176; A61B 2017/00792
See application file for complete search history.

(56) References Cited

U.S. PATENT DOCUMENTS

| | | | |
|---|---|---|---|
| 669,034 A | 2/1901 | Manly |
| 755,921 A | 3/1904 | O'Neill |
| 1,874,668 A | 8/1932 | Wadewitz |
| 2,665,692 A | 1/1954 | L'esperance |

(Continued)

FOREIGN PATENT DOCUMENTS

| | | |
|---|---|---|
| EP | 1598017 A1 | 11/2005 |
| EP | 1862125 A2 | 12/2007 |

(Continued)

OTHER PUBLICATIONS

Baumgarten and Wright, "Sliding Knots—Overhand Throw and Duncan Loop", *Arthroscopic Knot Tying—An Instruction Manual*, Lippincott, Williams & Wilkins, Philadelphia (2005), pp. 32 and 33.

(Continued)

*Primary Examiner* — Christine H Matthews
*Assistant Examiner* — Joshua D Lannu
(74) *Attorney, Agent, or Firm* — Panitch Schwarze Belisario & Nadel LLP

(57) ABSTRACT

A fabricated component for providing desired structural support has plural strands of material extending between opposing gathering points, and free ends extending from the gathering points. The component is preferably fabricated from a single strand of material using an appropriate folding procedure which includes the formation of plural loops of the strand, one upon the other, and development of the gathering points in opposing regions of the looped strand by passing opposing ends of the strand around the loops of the strand, and then through the resulting throws, or using a separate knotting arrangement. The fabricated component can be used in medical procedures, such as the support of subcutaneous tissue, muscle and organs, and other non-medical applications.

14 Claims, 9 Drawing Sheets

(56) References Cited

U.S. PATENT DOCUMENTS

| | | | |
|---|---|---|---|
| 2,860,902 A | 11/1958 | Diels | |
| 2,913,270 A | 11/1959 | Sachsenröder, Sr. | |
| 3,550,166 A * | 12/1970 | Kotler | A45F 3/22 |
| | | | 5/122 |
| 3,739,784 A | 6/1973 | Itoh | |
| 3,903,892 A | 9/1975 | Komiya | |
| 3,910,279 A | 10/1975 | Okada et al. | |
| 3,915,419 A * | 10/1975 | Brown | A47G 7/047 |
| | | | 248/318 |
| 4,008,912 A | 2/1977 | Kotov | |
| 4,306,561 A | 12/1981 | de Medinaceli | |
| 4,312,337 A | 1/1982 | Donohue | |
| 4,635,636 A | 1/1987 | Goldstein | |
| 4,638,802 A | 1/1987 | Okada | |
| 4,655,223 A | 4/1987 | Kim | |
| 5,224,488 A | 7/1993 | Neuffer | |
| 5,318,578 A | 6/1994 | Hasson | |
| 5,480,406 A * | 1/1996 | Nolan | A61B 17/0469 |
| | | | 289/1.2 |
| 5,569,271 A | 10/1996 | Hoel | |
| 5,624,446 A | 4/1997 | Harryman, II | |
| 5,645,548 A | 7/1997 | Augsburger | |
| 5,681,331 A | 10/1997 | de la Torre et al. | |
| 5,707,379 A | 1/1998 | Fleenor et al. | |
| 5,759,188 A | 6/1998 | Yoon | |
| 5,766,217 A | 6/1998 | Christy | |
| 5,776,150 A | 7/1998 | Nolan et al. | |
| 5,782,845 A | 7/1998 | Shewchuk | |
| D397,218 S | 8/1998 | Cadaver | |
| 5,807,276 A | 9/1998 | Russin | |
| 5,810,861 A | 9/1998 | Gaber | |
| 6,030,391 A | 2/2000 | Brainard et al. | |
| 6,035,967 A | 3/2000 | Maeda | |
| 6,036,700 A | 3/2000 | Stefanchik et al. | |
| 6,200,327 B1 | 3/2001 | Assal | |
| 6,347,816 B1 | 2/2002 | Donaho | |
| 6,638,286 B1 | 10/2003 | Burbank et al. | |
| 6,746,471 B2 | 6/2004 | Mortier et al. | |
| 6,749,615 B2 | 6/2004 | Burdulis et al. | |
| 6,770,084 B1 | 8/2004 | Bain et al. | |
| 6,835,193 B2 | 12/2004 | Epstein et al. | |
| 6,936,024 B1 | 8/2005 | Houser | |
| 7,101,378 B2 | 9/2006 | Salameh et al. | |
| 7,198,626 B2 | 4/2007 | Lee et al. | |
| 7,264,623 B2 | 9/2007 | Harris, Jr. et al. | |
| 7,322,939 B2 | 1/2008 | Burbank et al. | |
| 7,615,062 B2 | 11/2009 | Deland | |
| 7,771,441 B2 | 8/2010 | Cerundolo | |
| 7,918,868 B2 | 4/2011 | Marshall et al. | |
| 7,955,341 B2 | 6/2011 | Cerundolo | |
| 8,353,920 B2 | 1/2013 | Mikkaichi | |
| 2001/0025171 A1 | 9/2001 | Mortier et al. | |
| 2004/0102809 A1 | 5/2004 | Anderson | |
| 2004/0133216 A1 | 7/2004 | Wulc et al. | |
| 2004/0267270 A1 | 12/2004 | Jacobs et al. | |
| 2005/0261581 A1 | 11/2005 | Hughes et al. | |
| 2006/0004409 A1 | 1/2006 | Nobis et al. | |
| 2006/0004410 A1 | 1/2006 | Nobis et al. | |
| 2006/0025819 A1 | 2/2006 | Nobis et al. | |
| 2006/0069398 A1 | 3/2006 | Suzuki et al. | |
| 2006/0195007 A1 * | 8/2006 | Anderson | A61B 17/0401 |
| | | | 600/29 |
| 2006/0217762 A1 | 9/2006 | Maahs et al. | |
| 2006/0282100 A1 | 12/2006 | Pasricha et al. | |
| 2007/0118174 A1 | 5/2007 | Chu | |
| 2007/0179509 A1 | 8/2007 | Nagata et al. | |
| 2007/0293876 A1 | 12/2007 | Abe et al. | |
| 2008/0082113 A1 | 4/2008 | Bishop et al. | |
| 2008/0172085 A1 | 7/2008 | Chiu et al. | |
| 2008/0294185 A1 | 11/2008 | Blomdahl et al. | |
| 2009/0062817 A1 | 3/2009 | Suzuki et al. | |
| 2009/0082797 A1 | 3/2009 | Fung et al. | |
| 2009/0082805 A1 | 3/2009 | Kaiser et al. | |
| 2009/0216251 A1 | 8/2009 | Levine et al. | |
| 2009/0216268 A1 | 8/2009 | Panter | |
| 2010/0137679 A1 * | 6/2010 | Lashinski | A61B 17/0401 |
| | | | 600/37 |
| 2010/0331612 A1 | 12/2010 | Lashinski et al. | |
| 2011/0023696 A1 * | 2/2011 | Zeren | F41H 5/0471 |
| | | | 89/36.02 |
| 2012/0046693 A1 | 2/2012 | Denham et al. | |
| 2012/0059417 A1 | 3/2012 | Norton et al. | |
| 2012/0143225 A1 | 6/2012 | Chin et al. | |

FOREIGN PATENT DOCUMENTS

| | | |
|---|---|---|
| EP | 2238944 A2 | 10/2010 |
| EP | 2455002 A1 | 5/2012 |
| JP | S63-40559 A | 2/1988 |
| JP | H06-74146 U | 10/1994 |
| JP | H10-216161 A | 8/1998 |
| JP | 2001-198131 A | 7/2001 |
| JP | 2002-028164 A | 1/2002 |
| JP | 2004-513702 A | 5/2004 |
| JP | 2004-526483 A | 9/2004 |
| JP | 3628597 B2 | 3/2005 |
| JP | 2007-151615 A | 6/2007 |
| JP | 2007-167500 A | 7/2007 |
| JP | 2007-296319 A | 11/2007 |
| WO | 9406357 A1 | 3/1994 |
| WO | 9531149 A1 | 11/1995 |
| WO | 9602197 A1 | 2/1996 |
| WO | 9835616 A1 | 8/1998 |
| WO | 0239905 A1 | 5/2002 |
| WO | 03077771 A1 | 9/2003 |
| WO | 2005096956 A1 | 10/2005 |
| WO | 2006047563 A2 | 5/2006 |
| WO | 2007073931 A1 | 7/2007 |
| WO | 2008042992 A2 | 4/2008 |
| WO | 2008070691 A2 | 6/2008 |
| WO | 2009045248 A1 | 4/2009 |

OTHER PUBLICATIONS

"Knot Tying Illustrations—Easy Slider" and "Knot Tying Illustrations—The Fancy Slider"—Web Publication reviewed Oct. 13, 2010, at "www.utube.com/watch?v=ZJzf1LeQQck" and "www.phoenixsterling.com/IMAGES/Knot%20Tying%20Illustrations.pdf".

McMillan and Caspari, "Arthroscopic Knot-Tying Techniques", *An Atlas of Shoulder Arthroscopy*, Imhoff, Ticker and Fu, Editors, Martin Dunitz, London (2003), pp. 87 to 95.

Int'l Search Report and Written Opinion issued Oct. 30, 2014 in Int'l Application No. PCT/US2014/024816.

Office Action issued Jan. 14, 2014 in JP Application No. 2012-503414.

Partial translation of an Office Action issued Mar. 11, 2014 in MX Application No. MX/a/2010/001019.

Office Action issued Jul. 31, 2014 in AU Application No. 2010232964.

Office Action issued Jul. 31, 2014 in AU Application No. 2013204680.

Office Action issued Aug. 15, 2014 in AU Application No. 2013204057.

Office Action issued Sep. 9, 2014 in U.S. Appl. No. 12/384,326 by Levine.

Int'l Search Report and Written Opinion issued Aug. 28, 2014 in Int'l Application No. PCT/US2014/030533.

Office Action issued Jul. 10, 2014 in CA Application No. 2,694,650.

Office Action issued Oct. 16, 2014 in U.S. Appl. No. 12/452,743 by Levine.

Office Action issued Oct. 1, 2014 in IL Application No. 215256.

English translation of an Office Action issued Oct. 14, 2014 in MX Application No. MX/a/2010/001019.

Office Action issued Oct. 29, 2014 in KR Application No. 10-2010-7003741.

Office Action issued Dec. 18, 2012 in AU Application No. 2008307757.

(56) References Cited

OTHER PUBLICATIONS

Office Action issued May 10, 2013 in AU Application No. 2008307757.
Office Action issued Jul. 5, 2012 in U.S. Appl. No. 12/384,326.
Office Action issued Sep. 3, 2013 in U.S. Appl. No. 12/384,326 by Levine.
Office Action issued Feb. 27, 2013 in U.S. Appl. No. 12/452,743 by Levine.
Office Action issued Jul. 30, 2013 in U.S. Appl. No. 12/452,743 by Levine.
Office Action issued Jan. 27, 2015 in JP Application No. 2014-002445.
Int'l Preliminary Report on Patentability issued Feb. 6, 2015 in Int'l Application No. PCT/US2014/030533.
Office Action issued May 29, 2015 in U.S. Appl. No. 12/452,743 by Levine.
Search Report issued Mar. 27, 2015 in EP Applicaiton No. 08836569.7.
Office Action issued May 4, 2015 in IL Application No. 226164.
Office Action issued May 21, 2015 in CA Application No. 2,694,650.
English translation of an Office Action issued in MX Application No. MX/a/2010/001019.
Office Action issued Jun. 3, 2015 in U.S. Appl. No. 12/384,326 by Levine.
Office Action issued Sep. 29, 2015 in JP Application No. 2014-002445.
Int'l Preliminary Report on Patentability issued Sep. 24, 2015 in Int'l Application No. PCT/US2014/024816.
Int'l Search Report and Written Opinion issued Mar. 3, 2009 in Int'l Application No. PCT/US2008/009012.
Int'l Preliminary Report on Patentability issued Feb. 4, 2010 in Int'l Application No. PCT/US2008/009012.
Office Action issued Mar. 8, 2016 in MX Application No. MX/a12010/001019 (translation only).
Office Action issued May 2, 2016 in U.S. Appl. No. 12/452,743 by Levine.
Extended Search Report issued Oct. 14, 2016 in EP Application No. 14779952.2.

* cited by examiner

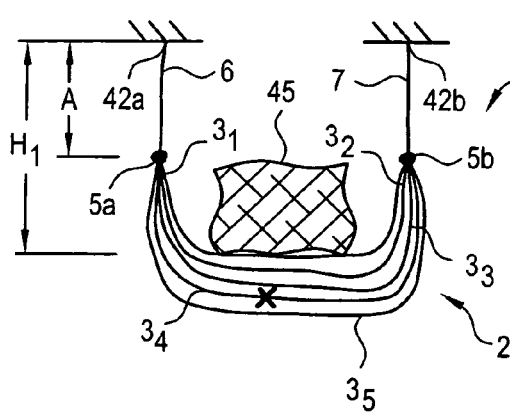
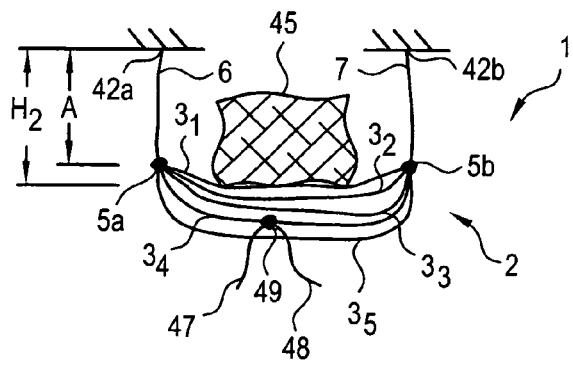
FIG. 21  FIG. 23
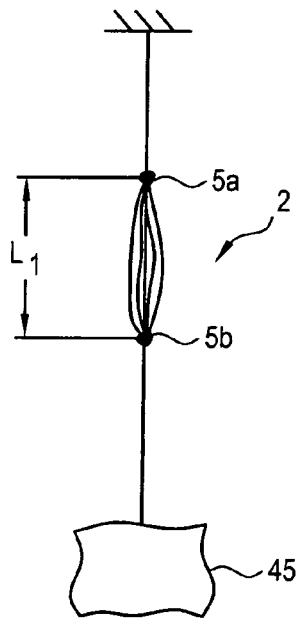
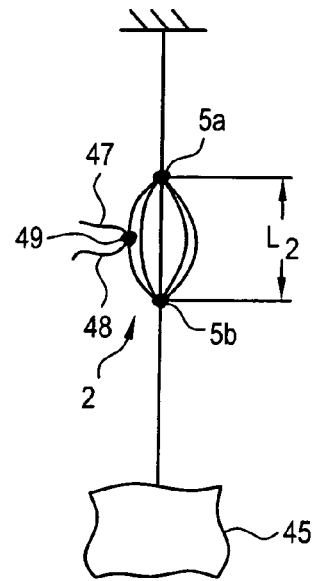
FIG. 22  FIG. 24

STRUCTURAL SUPPORT INCORPORATING MULTIPLE STRANDS

BACKGROUND OF THE INVENTION

The present invention generally relates to a fabricated component capable of use in supporting structural elements. The description which follows is primarily directed to uses of the fabricated component to support subcutaneous tissue, muscle and organs. It is to be understood, however, that the fabricated component is also capable of use in supporting various other structural elements.

Various devices have been proposed for use in supporting subcutaneous tissue, muscle and organs, particularly in applications where low stress is required to prevent damage or erosion of the engaged structures. As an example, in face lift procedures, tissue-supporting slings have been made using woven or braided components, primarily formed of suture materials. In practice, however, such devices have been unacceptable due to their bulk and stiffness, which could be annoying to a patient. Moreover, because such device are generally formed from a single strand of suture material, such devices have also been of concern because of the possibility of an erosion of such devices through tissue (i.e., a so-called "cheese-wire" effect).

Other proposed devices include barbs along a strand of suture material to provide additional support by engaging the tissue at one or more locations along the resulting component. In practice, however, such devices have also been troublesome because the barbs can pull away and can also feel prickly under the skin.

Pledgets have also been proposed for use in supporting internal organs but, in practice, are generally too bulky for use in supporting subcutaneous tissues, particularly facial tissues. Pledgets are also generally too large to be passed through small punctures in the skin and would, therefore, require open surgery for insertion.

SUMMARY OF THE INVENTION

In accordance with the present invention, these and other disadvantages are overcome by providing a multi-stranded component for providing desired structural support.

In a preferred embodiment, the multi-stranded component of the present invention has plural strands of material extending between opposing gathering points, and free ends extending from each of the gathering points. The plural strands of material preferably freely extend between the opposing gathering points so at least portions of the plural strands are brought into contact with one another. The free ends are each preferably formed of a single strand of material and are made suitable for desired manipulation in otherwise conventional manner. For use in applications such as the support of subcutaneous tissue, muscle and organs, the strands are preferably formed of suture materials useful in medical procedures, including metallic materials. Strands formed of other materials can be used in other, non-medical applications.

The multi-stranded component of the present invention can be fabricated in any of a variety of ways to suit any of a variety of desired applications. As is presently considered preferred, however, the multi-stranded component is fabricated from a single strand of suture material using an appropriate folding procedure. One such folding procedure includes the formation of plural loops of the strand, one upon the other. Opposing regions of the looped strand are then provided with gathering points, preferably by passing opposing ends of the strand around the loops, in each case forming at least one throw, and then through each of the resulting throws. As an alternative, the multi-stranded component can be fabricated from plural strands of suture material, once again using an appropriate folding procedure. One such folding procedure includes the formation of plural loops, one upon the other, with a first strand. Opposing regions of the looped strand are then provided with gathering points, preferably by tying additional strands of suture material around the loops.

The gathering points are preferably formed so that the engaged strands can slip within the gathering points, to allow the plural strands to slide relative to one another and to better conform to the shape of a region to be engaged. The gathering points can be drawn down, forming a closed loop structure, or can be tied off to form an open loop structure to facilitate sliding of the engaged strands relative to one another and relative to the gathering points. This can be used to develop open throws which can facilitate slippage of the engaged strands within the gathering points, to in turn facilitate sliding of the plural strands relative to one another.

The multi-stranded section can preferably adapt to the geometry of an engaged structure, including both curved and flat subcutaneous surfaces. Following fabrication, the plural strands extending between the gathering points will typically have a length corresponding to the region to be engaged, and will preferably become equally taut, for distribution of the load along the region to be engaged, such as tissue, muscle or an organ for the example of a medical procedure. This is particularly useful in the engagement of weak tissue. The ends of the fabricated component are preferably single-stranded, and are well suited to desired manipulations. The gathering points will be relatively small, and are well suited to passing through small structures and puncture points, and are easily tolerated because they are not bulky and are not sharp.

Such fabrication is sufficiently simple to allow the component to be fabricated without the need for special fasteners, and the resulting assembly cannot unravel during use. Using an assembly made of a contiguous strand, or plural strands of material prevents the assembly from breaking apart during use, or upon entry and removal. The fabricated component can be provided with features that can be located when hidden from view, and which can be referenced to other structures that may be hidden from view, for example, to bone, teeth or soft tissues in surgical applications.

Further description of the fabricated component, methods for fabricating the component, and uses of the fabricated component to support desired structures, is provided below, with reference to the following drawings.

BRIEF DESCRIPTION OF THE DRAWINGS

FIGS. 21 to 24 are schematic views illustrating modification of a fabricated component produced in accordance with the present invention to adjust the length of a fabricated component, in situ.

DETAILED DESCRIPTION OF PREFERRED EMBODIMENTS

Figure 1:
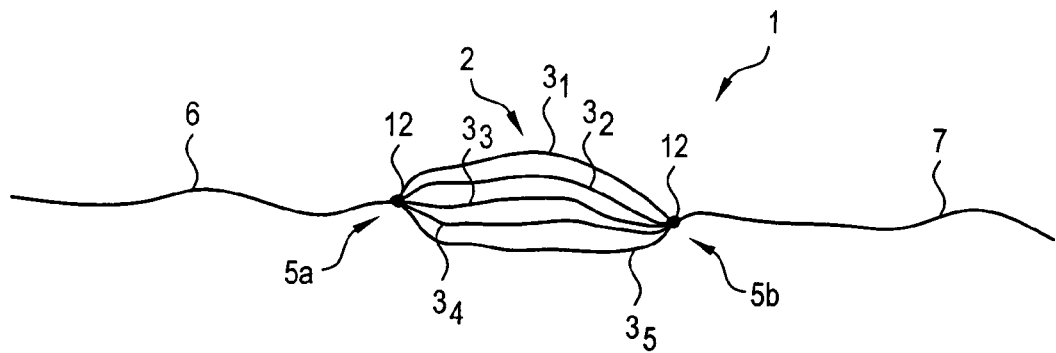
FIG. 1 is a plan view of an example of a fabricated component produced in accordance with the present invention.

FIG. 1 shows what is presently considered to be a preferred embodiment of the fabricated component 1 of the present invention. In this configuration, the center portion 2 of the component 1 is comprised of a plurality of strands $3_1$, $3_2$, $3_3$, $3_4$ and $3_5$. In the configuration selected for illustration in FIG. 1, a series of five strands $3_n$ has been employed. However, as will be understood from the discussion which is to follow, the center portion 2 can have any number of strands $3_n$, as preferred for a particular application. As an example, and for medical applications, a center portion having up to ten strands $3_n$ is presently considered to be preferred. The number of strands $3_n$ used in a particular application is preferably limited to the size of any openings or other structures through which the resulting component 1 is to pass.

The strands $3_n$ are each engaged by and extend between an opposing pair of gathering points $5a$, $5b$, and a free end 6, 7 extends from each of the gathering points $5a$, $5b$, as shown. Each of the gathering points $5a$, $5b$ preferably encircles a plurality of loops, as will be described more fully below, for stabilizing the fabricated component, and preferably bundles the strands and the plurality of loops together. To this end, the gathering points $5a$, $5b$ are preferably tied together, in each case forming a knot, or a plurality of knots, if appropriate for a particular application. The resulting knot preferably allows the plural strands $3_n$ to slip relative to one another and relative to the gathering points $5a$, $5b$, although fixed knots can also be used, if desired for a particular application. Knots useful for such purposes can be formed using a single throw, or multiple throws, as preferred, and the plural strands $3_n$ can have any of a variety of desired lengths. Plural strands $3_n$ having lengths on the order of 0.5 cm to 5 cm are presently considered preferred for medical/surgical applications such as tissue or muscle lifting or organ positioning.

Figure 2:
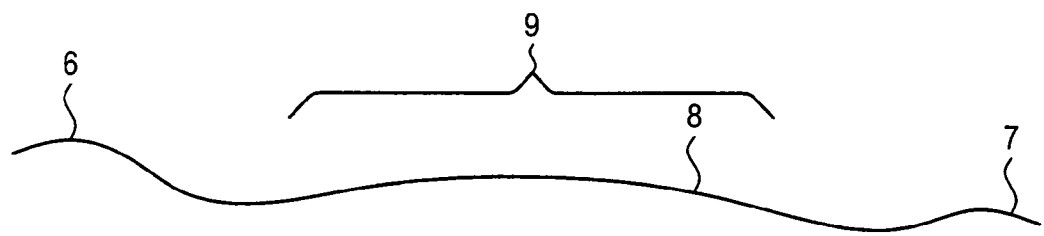
FIG. 2 is a plan view of a strand prior to the fabrication of a component produced in accordance with the present invention.

Fabrication of the component 1 shown in FIG. 1 will now be described with reference to FIGS. 2 to 4. Referring to FIG. 2, a strand 8 formed of a suitable material is provided, prior to fabrication. To facilitate fabrication and to prevent the resulting component 1 from separating during use, a unitary strand 8 is preferably used. As alternatives, the strand can be formed from a plurality of suitably joined strand sections, and multiple, preferably contiguous strands can be used instead of the single strand illustrated in FIG. 2. The strand 8 can be formed of any of a variety of suitable materials, which will depend on the application anticipated for the component 1 being fabricated. As an example, a conventionally available suture material is advantageously used in medical applications.

Figure 3:
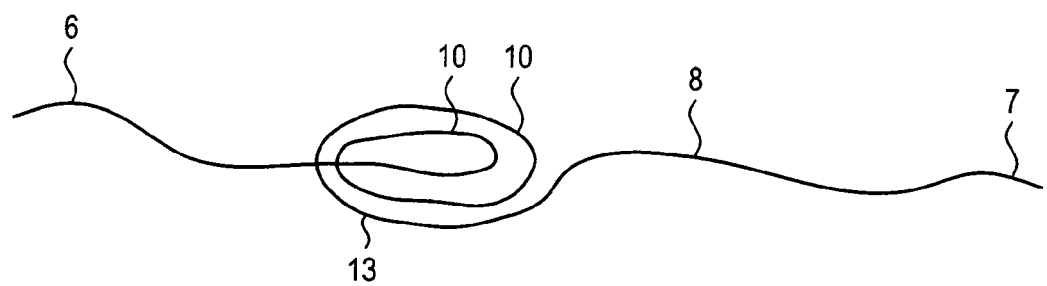
FIG. 3 is a plan view of the strand of FIG. 2, provided with a coiled portion during fabrication.

Referring next to FIG. 3, central portions 9 of the strand 8 are initially formed into a plurality of loops or coils $10_n$, including a half-section 13 for completion of the desired assembly as will be discussed more fully below. The coils $10_n$ can be round or oval in general shape, and can be formed with as many turns as is desired for a particular application. Two coils $10_n$, including the half-section 13 for completion of the assembly, have been selected for illustration for purposes of forming the series of five strands $3_1$, $3_2$, $3_3$, $3_4$, $3_5$ shown in FIG. 1. It is to be understood, however, that other numbers of coils $10_n$, for developing other numbers of strands $3_n$, can be used either in the configuration shown in FIG. 1, or in other desired configurations. In any event, the major diameter of the coiled loops will determine the length of the resulting, multi-stranded center portion 2.

Figure 4:
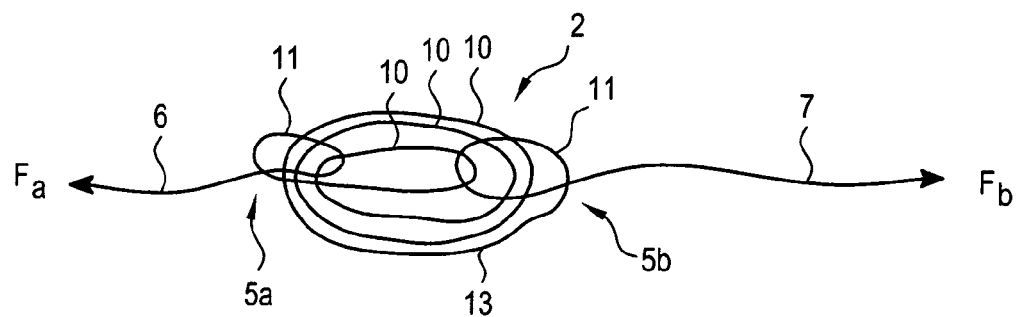
FIG. 4 is a plan view of the coiled strand shown in FIG. 3, provided with gathering points forming a closed loop at opposing regions of the coiled portion during fabrication.

Referring now to FIG. 4, each of the gathering points $5a$, $5b$ is then formed to complete fabrication of the component 1. This is preferably done by passing the opposing ends 6, 7 of the strand 8 around the bundle of coils $10_n$, in each case forming a throw 11, and by then passing the free ends 6, 7 of the strand 8 through each of the resulting throws 11, to hold the coils $10_n$ together. As an alternative, separate strands of material can be passed around the bundle of coils $10_n$ to hold the coils $10_n$ together, which can be used to develop free ends 6, 7 having a plurality of strands, if desired. Free ends 6, 7 having a plurality of strands can also be developed using a strand 8 formed from multiple strands, as previously described. As a further alternative, the free ends 6, 7 can be provided with loops, or looped portions, to facilitate the subsequent tying procedures which will be more fully described below, as well as broadened features, such as knots or beads, which can be used to provide support for the fabricated component which is normal to the ends 6, 7, when connected to desired attachment points. As a result, the lift axis established by the connected ends 6, 7 can be placed substantially normal to the supporting structure.

Each knot 12 resulting from the foregoing procedure is preferably tied to allow the plural strands $3_n$ to slide relative to one another and relative to the tied gathering points 5a, 5b. As a result, and when stretched by forces $F_a$ and $F_b$, the strands $3_n$ are allowed to slip into equal lengths, and the knots 12 are tightened to organized the strands $3_n$ into a suitably clustered array or web. In this way, the strands $3_n$ are provided with an equivalent length well suited to the equal support of a desired load. If, however, the support surface is slightly uneven, or warped, the lengths of the strands $3_n$ can readily adjust to such unevenness by sliding through the knots 12. As long as opposing forces are maintained, the resulting cluster will maintain its shape without unraveling. As an alternative, and if preferred for a particular application, an adhesive can be applied to the cluster, preferably at each of the knots 12, or a fixed knot can be used to maintain the resulting assembly in its desired configuration. Virtually any suture, string, cord, rope, metal component, or other strand, can be formed in this configuration.

In the configuration shown in FIG. 1, the knots 12 are drawn down, causing the throws 11 to contract into a closed loop structure which closely surrounds the engaged coils $10_n$ at each of the gathering points 5a, 5b. As an alternative, and referring to FIG. 5, the knots 12' can be tied off, as shown, to develop throws 11' forming a component 1' with an open loop structure having knots 12' spaced from the coils $10_n$. Providing throws 11' forming an open loop structure is presently considered preferred to facilitate sliding of the plural strands $3_n$ relative to one another and relative to the gathering points 5a, 5b. As a result, when stretched by forces $F_a$ and $F_b$, the strands $3_n$ are allowed to more easily slip into the equal lengths preferred to provide the strands $3_n$ with an equivalent length well suited to the equal support of a desired load.

Figure 5:
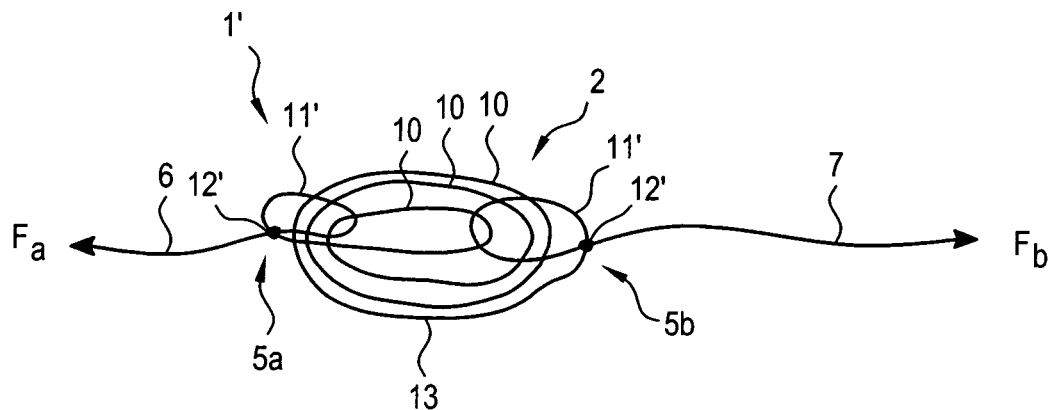
FIG. 5 is a plan view of the coiled strand shown in FIG. 3, provided with gathering points forming an open loop at opposing regions of the coiled portion during fabrication.
Figure 6:
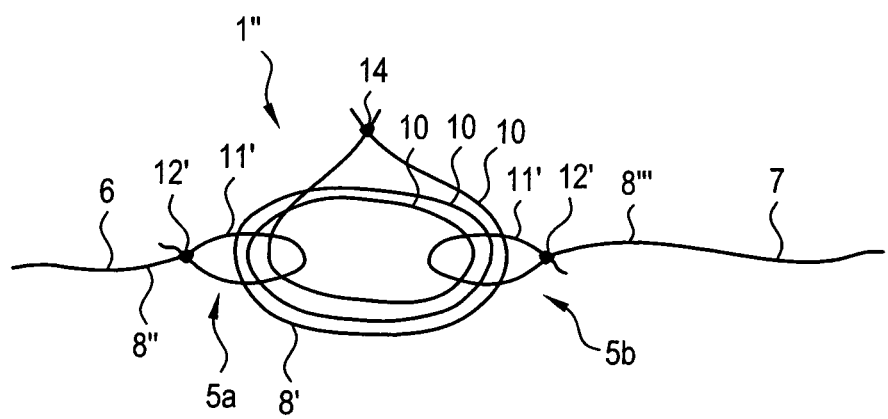
FIG. 6 is a plan view showing a fabricated component similar to the fabricated component shown in FIG. 5, which is formed from plural strands.

In the configurations shown in FIGS. 1 and 5, a unitary strand 8 is used to form the plurality of coils $10_n$, the gathering points 5a, 5b, and the free ends 6, 7. As a further alternative, multiple strands can be used to form the component 1" shown in FIG. 6. In this configuration, a first strand 8' similar to the strand 8 shown in FIGS. 1 and 5 is initially formed into a plurality of loops or coils $10_n$, similar to the coils $10_n$ shown in FIGS. 1 and 5 except that the half-section 13 is no longer needed for completion of the desired assembly. The ends of the first strand 8' are then knotted, at 14, to complete the coils $10_n$. Additional strands 8", 8"' formed of suitable materials, which can be the same material as the strand 8', or different materials, if preferred, are then used to form the opposing gathering points 5a, 5b, and the free ends 6, 7 extending from the gathering points 5a, 5b, as shown. Knots 12' can be used to form the open loop structures shown in FIG. 6, or the gathering points 5a, 5b can be drawn down to form closed loop structures, as desired. The fabricated component 1" shown in FIG. 6 is otherwise substantially similar to the fabricated components 1, 1' shown in FIGS. 1 and 5.

As a result of the foregoing, the plural strands $3_n$ will freely extend between the opposing gathering points 5a, 5b so that at least portions of the plural strands $3_n$ are brought into contact with one another. This is presently considered preferred to provide additional stress distribution along the center portion 2 of the fabricated component, for example, to provide additional stress distribution along engaged tissue in a medical procedure. This, in turn, provides additional support for engaged structures by enlarging the overall foot-print of the center portion 2, in situ, offering a greater distribution of forces.

Figure 7:
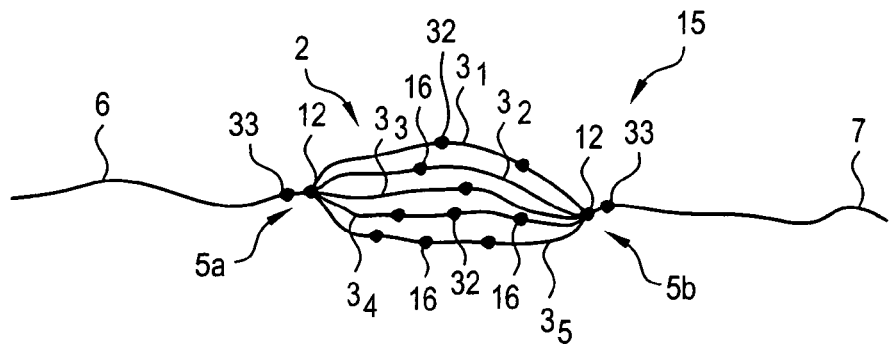
FIG. 7 shows an alternative embodiment fabricated component produced in accordance with the present invention, with gathering points forming a closed loop structure.
Figure 8:
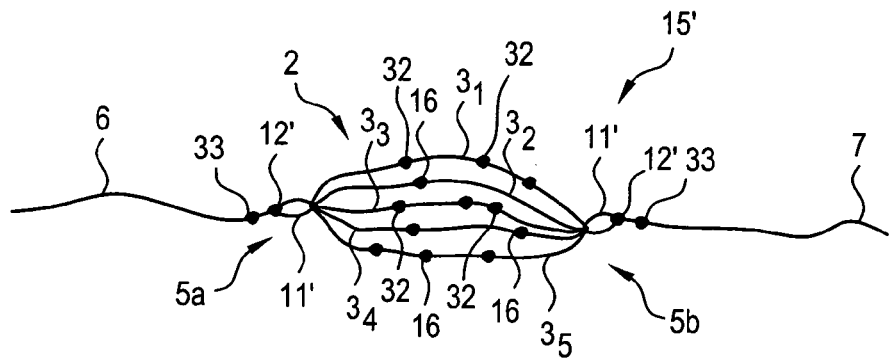
FIG. 8 shows the alternative embodiment fabricated component shown in FIG. 7, with gathering points forming an open loop structure.

FIGS. 7 and 8 show an alternative embodiment of a fabricated component 15, 15' produced in accordance with the present invention. In this configuration, the strands $3_1$, $3_2$, $3_3$, $3_4$, $3_5$ shown in FIGS. 1 and 5 have been provided with a plurality of knots 16. The fabricated component 15 of FIG. 7 is otherwise substantially similar to the fabricated component 1 shown in FIG. 1, and the fabricated component 15' shown in FIG. 8 is otherwise substantially similar to the fabricated component 1' shown in FIG. 5. An embodiment similar to the fabricated component 1" shown in FIG. 6 can also be produced, but is presently considered to be less preferred.

The knots 16 cause limited separation between the strands $3_1$, $3_2$, $3_3$, $3_4$, $3_5$ while allowing at least portions of the strands $3_1$, $3_2$, $3_3$, $3_4$, $3_5$ to remain in contact with one another. Limited separation of the strands $3_1$, $3_2$, $3_3$, $3_4$, $3_5$ can provide additional stress distribution along the center portion 2 of the fabricated component 15, 15', for example, to provide additional stress distribution along engaged tissue in a medical procedure. This can then provide additional support for engaged structures by enlarging the overall foot-print of the center portion 2, in situ, offering a greater distribution of forces. The knots 16 are preferably staggered along the lengths of the strands $3_1$, $3_2$, $3_3$, $3_4$, $3_5$, as shown, so that the knots 16 do not coincide and so that there is no unwanted bulk that might impede passage of the fabricated component 15, 15' through a narrow passage, such as punctures of the skin and subcutaneous passageways in medical applications.

Figure 9:
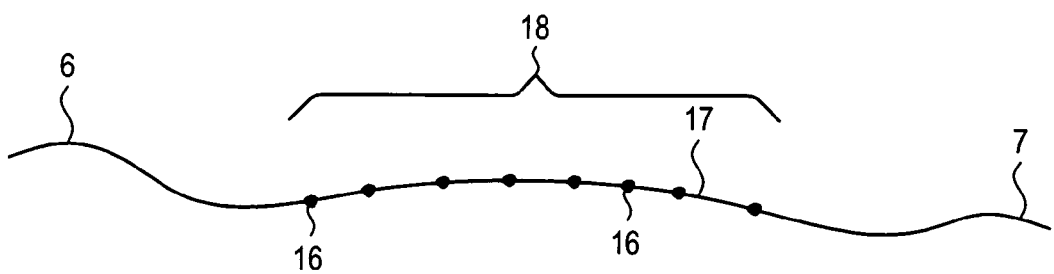
FIG. 9 is a plan view of an alternative embodiment strand for fabricating the components shown in FIGS. 7 and 8, having a plurality of knots formed in the strand.

Fabrication of the components 15, 15' shown in FIGS. 7 and 8 will now be described with reference to FIGS. 9 and 10. Referring to FIG. 9, a strand 17 similar to the strand 8 shown in FIG. 2 is provided with the knots 16, at desired locations along the strand 17, and which can vary to suit a particular application. This will include the locations of the knots 16, as well as the number of knots 16 formed along the strand 17. The knots 16 can either be uniform in size, and in overall configuration, or varied in size and in overall configuration, as is desired for a particular application. Typically, single throw knots will suffice for this, although multiple throw knots, thickened knots (e.g., a "figure-eight" configuration), or woven or braided knots can also be used.

Figure 10:
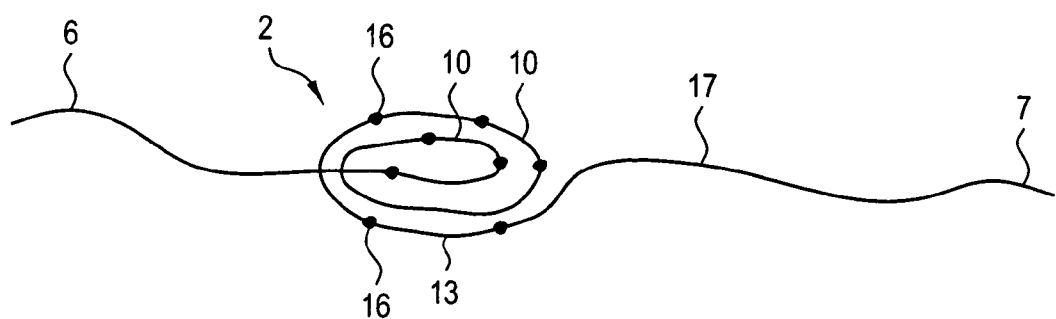
FIG. 10 is a plan view of the strand of FIG. 9, provided with a coiled portion during fabrication.

Referring next to FIG. 10, central portions 18 of the strand 17 are again initially formed into a plurality of loops or coils $10_n$, similar to the coils $10_n$ illustrated in FIG. 3. The knots 16 are preferably located along the length of the strand 17 so that the knots 16 will be located along the strands $3_1$, $3_2$, $3_3$, $3_4$, $3_5$ of the center portion 2 of the fabricated component 15, 15' following completion of the resulting assembly. Each of the gathering points 5a, 5b is then similarly formed to complete the fabrication of a closed looped component 15 or an open looped component 15', as desired. As a result of the foregoing, the knots 16 will typically be located as is shown in FIGS. 7 and 8, and each knot 16 can serve to separate portions of the strands $3_1$, $3_2$, $3_3$, $3_4$, $3_5$ from one another while other portions of the strands $3_1$, $3_2$, $3_3$, $3_4$, $3_5$ remain in contact with one another.

Figure 11:
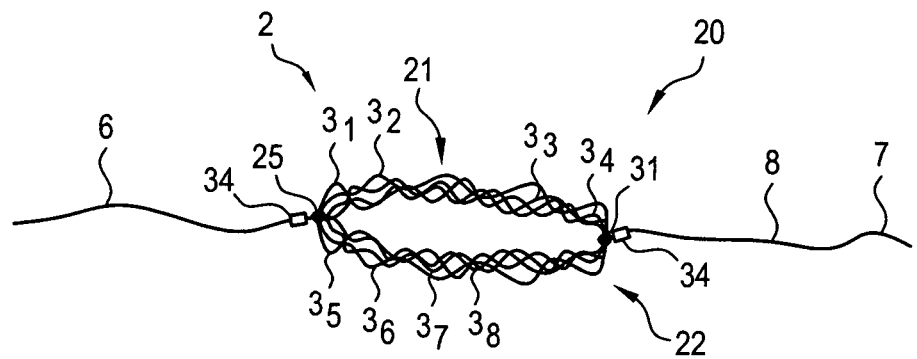
FIG. 11 is a plan view of a further alternative embodiment fabricated component produced in accordance with the present invention, with gathering points forming a closed loop structure.
Figure 12:
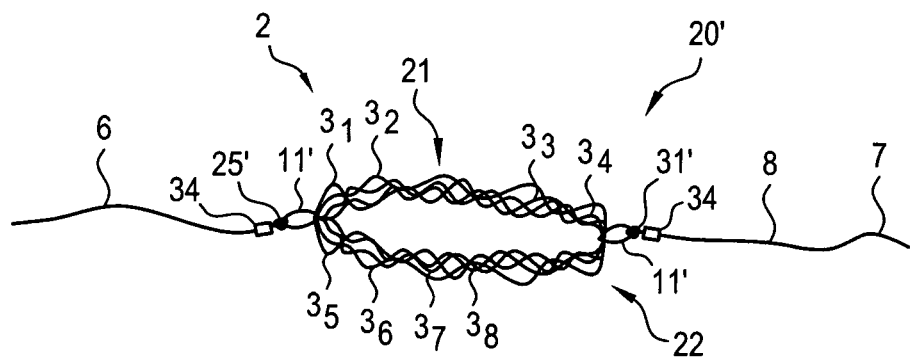
FIG. 12 shows the alternative embodiment fabricated component shown in FIG. 11, with gathering points forming an open loop structure.

FIGS. 11 and 12 show a further alternative embodiment of a fabricated component 20, 20' produced in accordance with the present invention. In this configuration, a series of eight strands $3_1$, $3_2$, $3_3$, $3_4$, $3_5$, $3_6$, $3_7$, $3_8$ have been organized into two separate groups 21, 22. Any number of strands $3_n$ can be combined into any of a number of separate groups, as is preferred for a particular application. Also in this configuration, the strands $3_1$, $3_2$, $3_3$, $3_4$ of the group 21 have been twisted together and the strands $3_5$, $3_6$, $3_7$, $3_8$ of the group 22 have separately been twisted together. It would also be possible, if desired, for all of the strands to be twisted together to form a single group. Twisting of the strands operates to further increase the overall bulk of the resulting assembly, providing another way of distributing stress along the center portion 2 of the fabricated component. The fabricated component 20 shown in FIG. 11 is otherwise substantially similar to the fabricated components 1, 15 shown in FIGS. 1 and 7, and the fabricated component 20' shown in FIG. 12 is otherwise substantially similar to the fabricated components 1', 15' shown in FIGS. 5 and 8. An embodiment similar to the fabricated component 1" shown in FIG. 6 can also be produced, but is presently considered to be less preferred.

Figure 13:
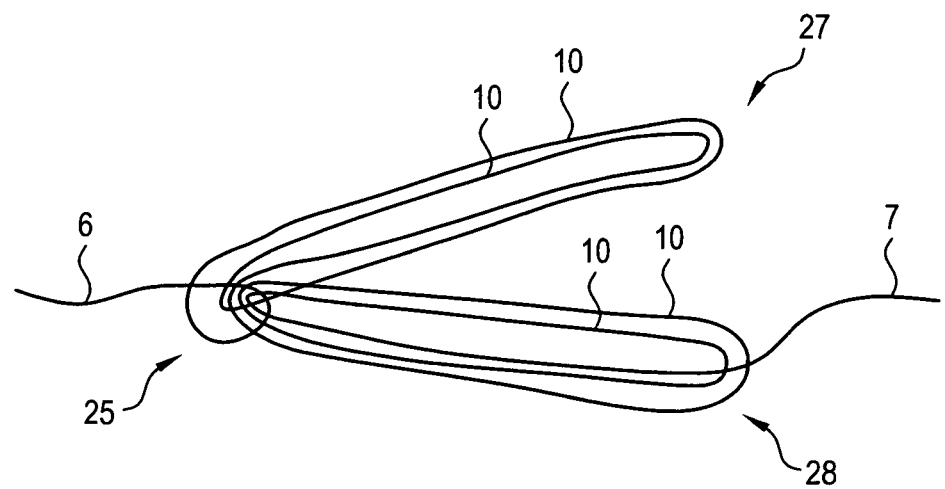
FIG. 13 is a plan view showing an intermediate step in the process for fabricating the alternative embodiment components shown in FIGS. 11 and 12.

Fabrication of the components 20, 20' shown in FIGS. 11 and 12 will now be described with reference to FIGS. 13 and 14. Referring to FIG. 13, a strand similar to the strand 8 shown in FIG. 2 is initially formed into a plurality of loops or coils $10_n$, similar to the coils $10_n$ shown in FIG. 3. A first gathering point 25 is then formed by passing one of the opposing ends 6 of the strand 8 around the bundled coils $10_n$, and then passing the end 6 of the strand 8 through the resulting throw, to hold the coils $10_n$ together. The coils $10_n$ are then divided into at least two groups, in the illustrated example, the groups 27 and 28.

Figure 14:
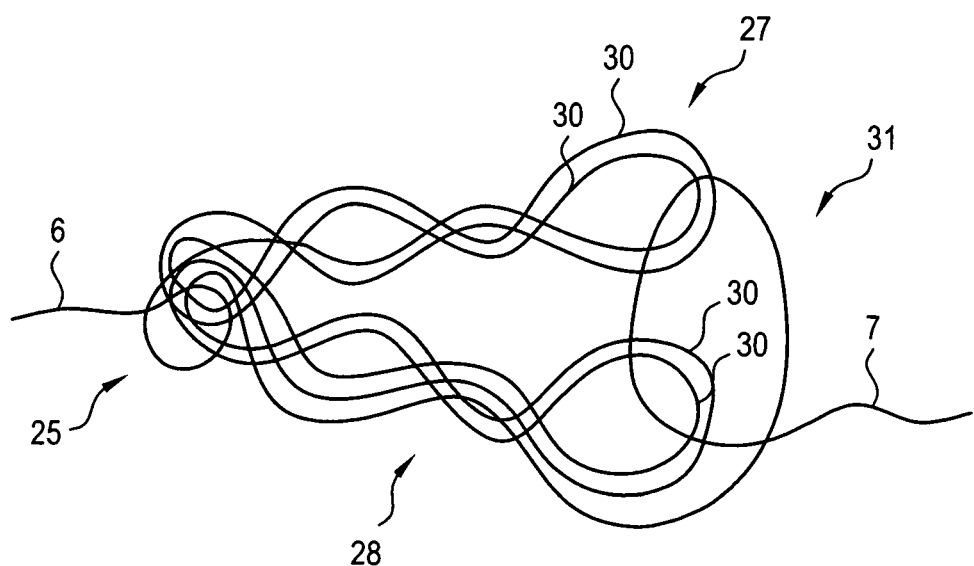
FIG. 14 is a plan view showing a subsequent step in the process for fabricating the alternative embodiment components shown in FIGS. 11 and 12.

Referring next to FIG. 14, the remaining free end 7 of the strand 8 is passed through free ends 30 of the coils $10_n$ in the first group 27, and is then passed through free ends 30 of the coils $10_n$ in the second group 28. A second gathering point 31 is then formed by joining the ends 30 of the coils $10_n$ in the first group 27 and the ends 30 of the coils $10_n$ in the second group 28. As previously described, the gathering point 31 can be formed by passing the end 7 of the strand 8 through the throw formed when joining the ends 30 of the coils $10_n$ in the first group 27 and the ends 30 of the coils $10_n$ in the second group 28, to hold the several coils $10_n$ together. Suitable formation of the second gathering point 31 results in fabrication of the component 20 shown in FIG. 11 or the component 20' shown in FIG. 12.

Figure 15:
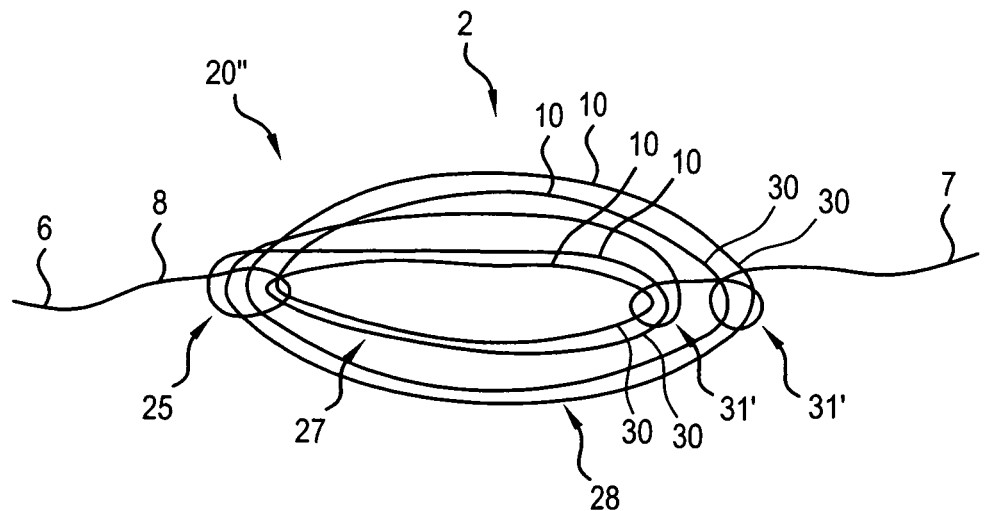
FIGS. 15 and 16 are plan views of further alternative embodiment fabricated components produced in accordance with the present invention, provided with plural gathering points formed at opposing regions of the coiled portion during fabrication.

FIG. 15 shows a further alternative embodiment of a fabricated component 20" produced in accordance with the present invention. In this configuration, a series of coiled loops $10_n$ have been organized into two separate groups 27, 28, similar to the previously described fabrication of the components 20, 20' shown in FIGS. 13 and 14. Any number of strands $3_n$ can be combined into any of a number of separate groups, as preferred for a particular application. In the configuration selected for illustration, the strands $3_n$ of the groups 27, 28 have not been twisted together. It would also be possible for some, or all of the strands and groups of strands to be twisted together as previously described, if desired.

A first gathering point 25 is formed, as previously described, by passing one of the opposing ends 6 of the strand 8 forming the component 20" around the bundled coils $10_n$, and by then passing the end 6 of the strand 8 through the resulting throw to hold the coils $10_n$ together. The remaining free end 7 of the strand 8 is first passed around the free ends 30 of the coils $10_n$ in the first group 27, and is passed through the resulting throw, causing the throw to contract into a closed loop structure which closely surrounds the engaged coils $10_n$ at a first gathering point 31'. A second gathering point 31' is then formed by passing the free end 7 of the strand 8 around the free ends 30 of the coils $10_n$ in the remaining group 28, and through the resulting throw, to again cause the throw to contract into a closed loop structure which closely surrounds the engaged coils $10_n$, and to complete the fabrication of the component 20". As a further alternative, the resulting throws can be knotted, similar to the knots 12' used to fabricate the components 1', 1", 15', 20', to form a component 20" having the open loop structures which are presently considered preferred to facilitate sliding of the plural strands $3_n$ relative to one another and relative to the gathering points 25, 31'.

The gathering points 31' are preferably staggered so they do not coincide and so that there is no unwanted bulk that might impede passage of the fabricated component 20" through a narrow passage, such as punctures of the skin and subcutaneous passageways in medical applications. For this reason, the size of the coils $10_n$ which form the group 27 preferably differs from the size of the coils $10_n$ which form the group 28.

Figure 16:
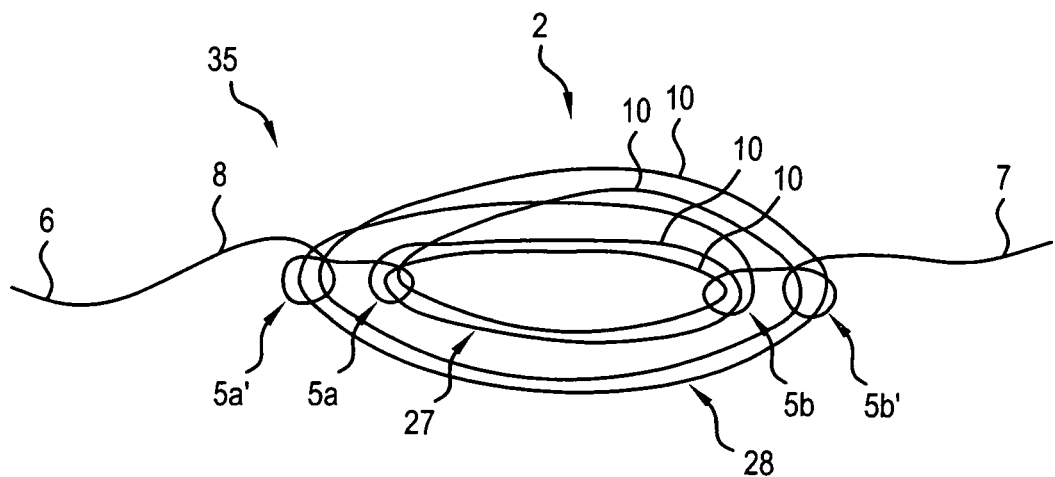

FIG. 16 shows a further alternative embodiment of a fabricated component 35 produced in accordance with the present invention, having plural gathering points at each of the opposing ends of the center portion 2. The component 35 can be fabricated using a strand of material which is similar to the strand 8 used to form other embodiments, but having an increased length. One end of the strand 8 is used to form a group 27 of bundled coils $10_n$, similar to the coils $10_n$ used to form the components 1, 1', 1" shown in FIGS. 3 to 6. Two gathering points 5a, 5b are then formed, for example, by passing opposing portions of the strand 8 around the bundle of coils $10_n$ forming the group 27, in each case forming a throw, and by then passing available portions of the strand 8 through each of the resulting throws to hold the coils $10_n$ together, as previously described. The remainder of the strand 8 can then be used to form another group 28 of bundled coils $10_n$, similar to the group 27. Two additional gathering points 5a', 5b' can then be formed, for example, by passing opposing portions of the strand 8 around the bundle of coils $10_n$ forming the group 28, in each case forming a throw, and by then passing available portions of the strand 8 through each of the resulting throws to hold the coils $10_n$ together and complete the fabrication of the component 35. The gathering points 5a, 5a' and the gathering points 5b, 5b' are preferably staggered relative to one another so the various gathering points do not coincide and so that there is no unwanted bulk that might impede passage of the fabricated component 35 through a narrow passage, such as punctures of the skin and subcutaneous passageways in medical applications.

Any number of strands $3_n$ can be combined into any of a number of separate groups, as is preferred for a particular application. In addition, and as a further alternative, separate strands of material can be passed around the bundles of coils $10_n$ to hold the coils $10_n$ together, which can be used to develop free ends 6, 7 having a plurality of strands, if desired. Free ends 6, 7 having a plurality of strands can also be developed using a strand 8 formed from multiple strands, as previously described. Also, while the groups 27, 28 of strands $3_n$ have not been twisted together in the configuration illustrated, it would be possible for some, or all of the strands and groups of strands to be twisted together as previously described, if desired.

A series of single throw ties can be used to form the gathering points 5a, 5b of the components 1, 1', 15, 15', the gathering points 25, 25' and 31, 31' of the components 20, 20', 20", and the gathering points 5a, 5a' and 5b, 5b' of the component 35, if desired, and would preferably be used to form the knots 12' of the component 1", or to further secure the knots 12, 12' and prevent the gathering points from unraveling. Multiple throws, preferably forming square knots, are currently considered to be particularly useful.

Because the various fabricated components which have previously been described are particularly well suited to uses supporting subcutaneous tissue, muscle and organs, or other structures which may be hidden from view, certain uses could benefit from structures which would help locate the component during use and when hidden from view. This can be accomplished by providing the fabricated component with features that can be located when hidden from view, and which can be referenced to other structures that may be hidden from view, for example, to bone, teeth or soft tissues in surgical applications.

For example, the knots 16 of the components 15, 15' shown in FIGS. 7 and 8 can be replaced with beads formed of a material that can be suitably detected. As an alternative, beads 32, 33 formed of a detectable material can additionally be positioned as is shown in FIGS. 7 and 8. The beads 32 are positioned between adjacent knots 16, and are retained in desired position by the knots 16. The beads 33 are positioned adjacent to and outboard from the knots 12, 12', and can be retained in position by suitably knotting the free ends 6, 7 of the strand 8 over the beads 33. As a further alternative, cylinders 34 formed of a detectable material can be used, as is shown, for example, in FIGS. 11 and 12, adjacent to and outboard from the knots 25, 31 or the knots 25', 31'. The beads 33 and the cylinders 34 can be located on both sides of the center portion 2, as is shown in the drawings, or can be located on either of the two sides, if preferred for a given application, for example, to locate the left or right side of the component. The beads 32, 33 and the cylinders 34 can be retained in position by knots, as previously described, or can be retained in position using an adhesive, or mechanically, for example, by crimping.

The beads 32, 33, and the cylinders 34, can be formed of any material which can be appropriately detected by equipment suited to the use being undertaken with the fabricated component. For example, metallic structures or other materials which are opaque to x-ray equipment or ultrasound equipment can be used. Stainless steel would be well suited to surgical applications. However, any material suitable to detection by an appropriate technology can be used to achieve a similar result. The beads 32, 33 can be spherical or oval, and the cylinders 34 can be shaped, as may be needed to provide a suitably detectable structure. Sizes on the order of 21 to 23 gage, or 1 mm in diameter or length, are presently considered to be preferred.

Examples of some applications using the fabricated components which have previously been described will now be illustrated. These illustrative applications are described in the context of a medical procedure of the type described, for example, in U.S. patent application Ser. No. 12/452,743 and in U.S. patent application Ser. No. 12/384,326, the subject matter of which is incorporated by reference as if fully set forth herein. It is to be understood, however, that the fabricated components of the present invention can also be used to perform other medical procedures, as well as other non-medical procedures suited to a particular application. The fabricated components of the present invention can also be used in place of a conventional suture, to perform any of a variety of medical procedures, with or without the placement of a needle at either or both of the ends 6, 7 of the fabricated component, as is desired for a given application.

Figure 17:
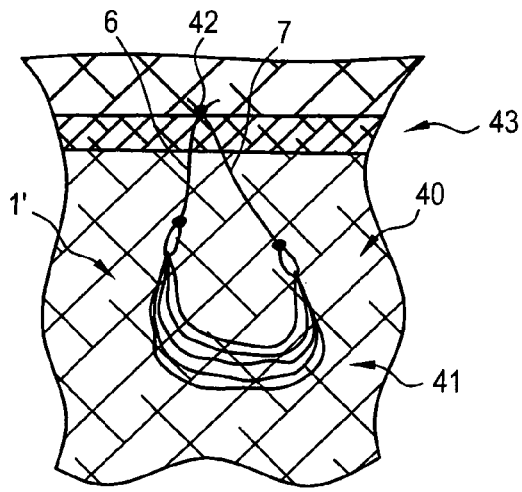
FIGS. 17 to 19 are schematic views showing an application of the alternative embodiment components shown in FIGS. 5, 8 and 12, respectively, in situ.
Figure 18:
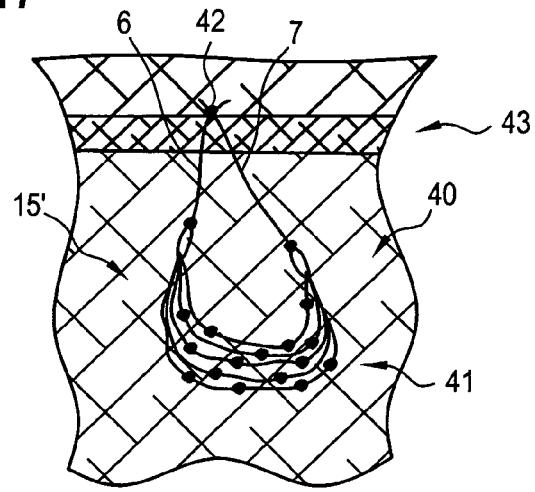
Figure 19:
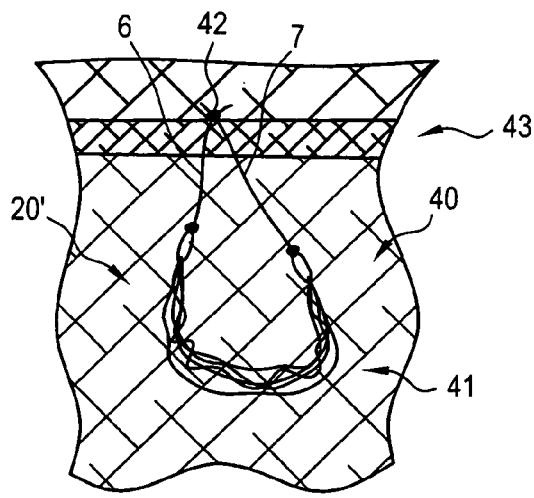

In a first illustrative example, and referring to FIGS. 17, 18 and 19, the components 1', 15', 20' respectively illustrated in FIGS. 5, 8 and 12 are shown in use performing a mid face surgical application in which the malar fat pad 40 has been engaged by a suture-supporting sling 41. The sling 41 is positioned subcutaneously, under the malar fat pad 40, and is engaged and anchored at 42, for example, in or above the bone or periosteum in the zygomatic arch 43. It is to be understood that while the opposing ends 6, 7 of the components 1', 15', 20' have been anchored in the same location, the ends 6, 7 can also be anchored at separate locations, if preferred.

Figure 20:
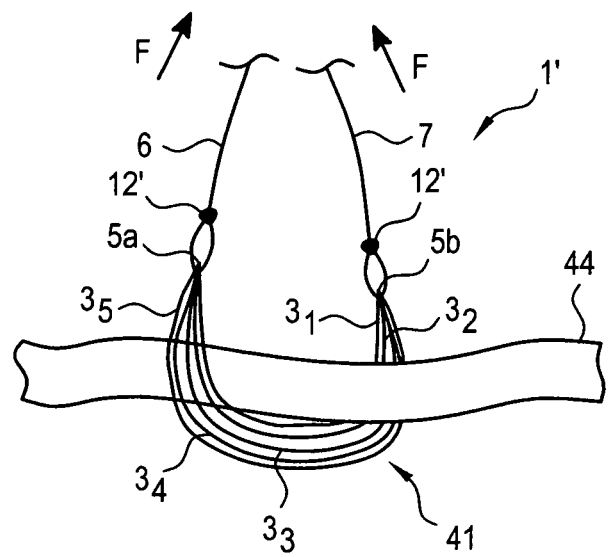
FIG. 20 is a schematic view showing use of the alternative embodiment component shown in FIG. 5 to support a duct, vessel or organ, in situ.

In another illustrative example and referring to FIG. 20, the component 1' illustrated in FIG. 5 is shown in use for the suspension of a vessel 44, or other organ, using a sling 41 developed by multiple strands $3_1$, $3_2$, $3_3$, $3_4$, $3_5$ of the component 1', appropriately supported by the ends 6, 7 of the component 1', which is schematically illustrated by the vectors F.

It should be noted that for purposes of illustration, the multiple strands $3_1$, $3_2$, $3_3$, $3_4$, $3_5$ have been separated to more clearly illustrate the structures of the components being shown in FIGS. 17 to 20. In practice, however, the strands $3_1$, $3_2$, $3_3$, $3_4$, $3_5$ of such components would be bunched together, between their opposing gathering points, so that at least portions of the strands $3_1$, $3_2$, $3_3$, $3_4$, $3_5$ are in contact with one another.

In use, the multiple strands $3_1$, $3_2$, $3_3$, $3_4$, $3_5$ of the sling 41 act as a cushion for protecting the engaged structure from high stress damage or erosion. For strands $3_1$, $3_2$, $3_3$, $3_4$, $3_5$ capable of sliding within the gathering points 5a, 5b of the component, the plural strands $3_n$ will remain equally taut so the load will be evenly distributed. The thickened bundle presented by the plural strands $3_1$, $3_2$, $3_3$, $3_4$, $3_5$ eliminates the need to use larger diameter strands to achieve a similar result, which could otherwise introduce an unacceptable stiffness to the positioned sling 41.

In some applications, there can be a need to adjust a component which has been positioned, subsequent to placement of the component. For example, in conjunction with the previously described surgical procedures, there is the potential for the positioned component to migrate, or for there to be a change in the condition of the tissue, muscle or organ engaged by the component, leading to the potential for there to be an erosion through the engaged tissue, muscle or organ. In such cases, the ability to adjust the component after the component has been subcutaneously placed would avoid the need for open surgery to remove or replace the component.

Such adjustment is preferably achieved in accordance with the present invention by adjusting the length of one or more of the strands $3_n$ of the positioned component. For example, FIG. 21 schematically shows a mass 45 supported by the strands $3_n$ of the center portion 2 of the component 1 shown in FIG. 1. As an example, the mass 45 can represent subcutaneous malar fat in a face lift procedure, supported by anchoring points 42a, 42b formed at spaced locations along the bone or periosteum in the zygomatic arch. FIG. 22 shows a corresponding diagram illustrating the forces involved. The center portion 2 has an initial length $L_1$ and is spaced from the anchoring points 42a, 42b by a distance A, yielding an initial lift height $H_1$.

Adjustment of the assembly is accomplished by changing the length of the center portion 2. To this end, and referring to FIGS. 23 and 24, which correspond to the FIGS. 21 and 22, respectively, at least one of the strands $3_n$ has been shortened.

In the illustrated example, the strand $3_4$ has been shortened by cutting the strand $3_4$ and by suitably connecting the cut ends 47, 48 of the strand $3_4$ at a different location, shown at 49. This can be done by knotting the free ends, by using a separate tie to reconnect the free ends, or by using a separate band or clip to join the free ends. Additional shortening of the strand $3_4$ can be accomplished by removing a portion of the cut strand, prior to reconnection. Adjustments such as the foregoing can be performed by severing a single strand, or by severing plural strands, if desired. If plural strands are to be adjusted, a separate connection 49 can be associated with each of the strands, or a single connection 49 can be associated with multiple strands.

Figure 25:
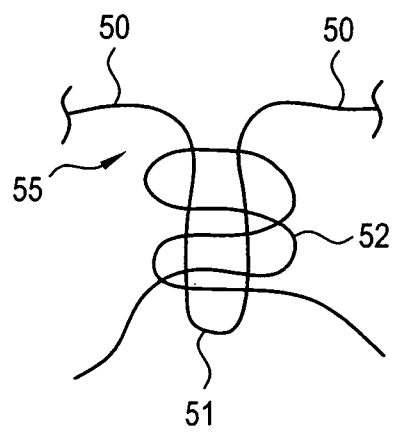
FIGS. 25 and 26 are side elevational views showing alternative techniques for adjusting the length of a fabricated component produced in accordance with the present invention.
Figure 26:
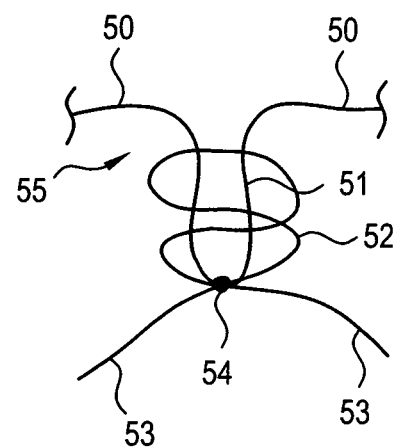

It is also possible to shorten the strand $3_4$ without cutting the strand $3_4$, but to instead knot or otherwise gather the strand $3_4$ at the location 49, or to use a separate tie, band or clip to engage the strand $3_4$ at the location 49. As an example, and referring to FIGS. 25 and 26, the strand 50 has not been cut, but has instead been gathered to form a loop 51. Referring to FIG. 25, a separate tie 52 is placed around, or in the alternative, woven through the exposed loop 51. Referring next to FIG. 26, the ends 53 of the tie 52 are preferably knotted, braided, banded or clipped at the location 54 to prevent the loop 51 from unraveling and to maintain the shortened length established for the strand 50. As an alternative, the strand 50 can be joined at other locations along the loop 51, for example, along the upper portions 55. Among other applications, such configurations can be useful in situations where cut ends would be too short to effectively receive a knot, but would be of a sufficient length to receive the tie 52, including both medical and non-medical applications.

Any strands $3_n$ which have not been cut or otherwise shortened will then preferably slip through the gathering points 5a, 5b (or the gathering points 25, 31) to equalize the resulting assembly. To be noted is that for procedures such as the above mentioned face lift procedures, the foregoing operations can be performed on a subcutaneously located component, by drawing the strand or plural strands to be adjusted through a puncture point at or near the location 49, avoiding the need for open surgery to remove or replace the component.

As a result of the foregoing operations, and referring to FIGS. 23 and 24, the center portion 2 will have a reduced length $L_2$. Because the center portion 2 will remain spaced from the anchoring points 42a, 42b by the distance A, this will yield a final lift height $H_2$ which is shorter than the initial lift height $H_1$. Such adjustment can be used to suitably reposition the supported mass 45, for example, to raise the malar fat in the foregoing example of a face lift procedure.

Because the strands $3_n$ are permitted to slip within the gathering points 5a, 5b and 25, 31, a mechanical reduction (1:n) will result from shortening of the strands. This yields greater sensitivity to adjustment, increasing the precision in control of the change in length and facilitating lift of the supported mass 45. As an example, for the array of five strands $3_1, 3_2, 3_3, 3_4, 3_5$ previously discussed, shortening one of the strands will yield a 1:5 reduction for the resulting array. This, in turn, yields a corresponding increase in the working length of the shortened strand, allowing a knot or other suitable connection to be more easily formed. Such effects can be even further amplified by adjusting plural strands forming the array and/or by increasing the number (n) of strands associated with the array, if desired for a particular application. To accommodate such effects, the center portion of a fabricated component is preferably initially formed to be longer than the structure to be supported so that in the event the center portion is later to be shortened, a surplus working length will be available for shortening of the strands $3_n$ without interfering with the supported structure, for purposes of yielding a smooth and more even result.

Adjustment procedures such as the foregoing, including adjustments involving cut strands or looped strands, can be used to adjust the previously described fabricated components, as well as other desired components, including conventional sutures used in various medical procedures and surgical applications. This can include the adjustment of exposed components, as well as the adjustment of unexposed components such as subcutaneously located sutures and the like. As an example, a subcutaneously positioned suture can be adjusted by engaging the suture through a puncture point or a small opening, and by pulling the suture through the puncture point, exposing the suture for adjustment as previously described. The adjusted suture can then be pushed through the opening which, because of its small size, can easily heal in the normal course. Such adjustment can be used to later correct a surgical procedure, either to achieve an improved result or to provide for changes occurring following the surgical procedure due, for example, to migration or aging of the engaged tissues or the previously positioned component, without the need to replace the original component or for any open surgery.

It will be understood that while the present invention has been described based on specific embodiments incorporating specified parts, the present invention further encompasses all enabled equivalents of the parts described, and that various changes in the details, materials and arrangement of parts which have been herein described and illustrated in order to explain the nature of this invention may be made by those skilled in the art within the principle and scope of the invention as expressed in the following claims.

What is claimed is:

1. A component for providing structural support to a mass, comprising:
    a central strand section of material forming multiple loops to support the mass, a first bundle of the multiple loops passing through a first gathering point encircling the first bundle, and a second bundle of the multiple loops passing through a second gathering point encircling the second bundle, the multiple loops freely extending between the first and second gathering points, wherein at least one of the first and second gathering points comprises an end of the central strand section looping around the first or second bundle, respectively, thereby forming a throw, and passing through the throw;
    a first end strand section of material forming a first free end of the component and being connected to the central strand section; and
    a second end strand section of material forming a second free end of the component and being connected to the central strand section.

2. The component of claim 1 wherein the multiple loops are freely slidable around the first and second gathering points to slip relative to one another.

3. The component of claim 1 wherein the central strand section, the first end strand section and the second end strand section are formed from a single strand of material.

4. The component of claim 1 wherein the central strand section, the first end strand section and the second end strand section are formed from a plurality of individual strands of material.

5. The component of claim 1 wherein at least one of the first and second gathering points further comprises the first end strand section.

6. The component of claim 1 wherein the central strand section, the first end strand section and the second end strand section are formed of a suture material useful in a medical procedure.

7. The component of claim 1 which further includes an adhesive applied to at least one of the first and second gathering points.

8. The component of claim 1 which further includes a marker coupled with the component for locating a portion of the component which is at least partially hidden from view.

9. The component of claim 8 wherein the marker is a bead or a cylinder coupled with the strands of the component.

10. The component of claim 8 wherein the marker is a bead or a cylinder coupled with at least one free end of the component.

11. The component of claim 8 wherein the marker is formed of a material that can be detected by x-ray equipment or ultrasound equipment.

12. The component of claim 1, wherein at least one of the first and second gathering points further comprises the second end strand section.

13. The component of claim 1, wherein at least one of the first and second gathering points is formed from the central strand section.

14. The component of claim 1, wherein the first gathering point further comprises the first end strand section and the second gathering point further comprises the second end strand section.

* * * * *